United States Patent [19]

Huang et al.

[11] Patent Number: 4,874,902
[45] Date of Patent: Oct. 17, 1989

[54] METHOD FOR THE PREPARATION OF FLUOROMETHYL 1,1,1,3,3,3-HEXAFLUORO-2-PROPYL ETHER

[75] Inventors: Chialang Huang, Edison; Gerald G. Vernice, Nutley, both of N.J.

[73] Assignee: BOC, Inc., New Providence, N.J.

[21] Appl. No.: 196,712

[22] Filed: May 20, 1988

[51] Int. Cl.$^4$ .............................................. C07C 41/22
[52] U.S. Cl. .................................... 568/683; 568/684
[58] Field of Search ................................ 568/683, 684

[56] References Cited

U.S. PATENT DOCUMENTS

| | | | |
|---|---|---|---|
| 3,527,814 | 9/1970 | Croix et al. | 568/683 |
| 3,683,092 | 8/1972 | Regan et al. | 568/683 |
| 3,911,024 | 10/1975 | Croix | 568/683 |
| 3,976,788 | 8/1976 | Regan | 568/683 |

OTHER PUBLICATIONS

E. F. Mooney—"An Introduction to $^{19}$F NMR Spectroscopy", 1970—p. 9.

Yuminov et al., Translation from Zhurnal Obshchei Khim., vol. 37, pp. 375-380, 1967.

*Primary Examiner*—Howard T. Mars
*Attorney, Agent, or Firm*—R. Hain Swope; Larry R. Cassett

[57] ABSTRACT

Fluoromethyl 1,1,1,3,3,3-hexafluoro-2-propyl ether is prepared by reacting bromine trifluoride and methyl 1,1,1,3,3,3-hexachloro-2-propyl ether or chloromethyl 1,1,1,3,3,3-hexachloro-2-propyl ether. The mixed fluorochloro ether intermediates having the formula of

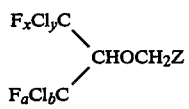

(wherein $x+y=3$, $a+b=3$, and $Z=H$ Cl, or F) are converted to fluoromethyl 1,1,1,3,3,3-hexafluoro-2-propyl ether by reactions with bromine trifluoride.

2 Claims, No Drawings

METHOD FOR THE PREPARATION OF FLUOROMETHYL 1,1,1,3,3,3-HEXAFLUORO-2-PROPYL ETHER

BACKGROUND OF THE INVENTION

This invention relates to the preparation of fluoromethyl 1,1,1,3,3,3-hexafluoro-2-propyl ether, which is also known as sevoflurane.

Sevoflurane is an inhalation anesthetic agent, first disclosed in U.S. Pat. Nos. 3,476,860 and 3,689,571. Sevoflurane exhibits rapid induction and recovery compared to halothane. Although unstable to soda lime, sevoflurane may have use in countries such as Japan which do not employ a closed breathing circuit comprising soda lime.

Several methods have been disclosed for preparing sevoflurane. For example, according to Regan et al., U.S. Pat. No. 3,689,571, sevoflurane may be made by photochemical chlorination of methyl 1,1,1,3,3,3-hexafluoro-2-propyl ether, of which the preparation is disclosed in U.S. Pat. No. 3,346,448, to produce chloromethyl 1,1,1,3,3,3-hexafluoro-2-propyl ether, followed by a substitution reaction with potassium fluoride in solvent. Alternatively, sevoflurane may be made by fluorination of methyl 1,1,1,3,3,3-hexafluoro-2-propyl ether with bromine trifluoride, or by the combined reaction of 1,1,1,3,3,3-hexafluoro-2-propanol, paraformaldehyde and anhydrous hydrogen fluoride followed by heating the product with excess anhydrous hydrogen fluoride. A method involving the reaction of methyl 1,1,1,3,3,3-hexafluoro-2-propyl ether and bromine trifluoride is also disclosed in *Zh. Obshch. Khim.*, vol. 37, pp. 375–380 (1967) and *Chem. Abstracts*, vol. 67, No. 43357x. Another method, which represents an improved reaction of 1,1,1,3,3,3-hexafluoro-2-propanol, paraformaldehyde and hydrogen fluoride, is disclosed in U.S. Pat. No. 4,250,334, which discloses using concentrated sulfuric acid and continuously collecting product vapors in a cold collector. This continuous method is improved further as disclosed in U.S. Pat. No. 4,469,898, which discloses adding 1,1,1,3,3,3-hexafluoro-2-propanol to a preformed mixture of formaldehyde, hydrogen fluoride and a dehydrating, protonating and fluoride ion generating agent. Another method for preparing fluoromethyl 1,1,1,3,3,3-hexafluoro-2-propyl ether is disclosed in U.S. Pat. No. 3,897,502. In this method, methyl 1,1,1,3,3,3-hexafluoro-2-propyl ether is reacted with fluorine in argon and Freon E-3 to produce sevoflurane.

The methods mentioned above involve the use of relatively expensive starting materials, notably 1,1,1,3,3,3-hexafluoro-2-propanol or the very toxic hexafluoroacetone. The manufacturing cost of the final product is therefore commensurately higher.

It has been known that bromine trifluoride is able to replace a halogen atom, other than fluorine, by a fluorine atom. For example, A. A. Banks et al., in *J. Chem. Soc.*, 2188 (1948), disclose the reaction of bromine trifluoride and carbon tetrahalide (except fluoride) to produce carbon monofluoro and carbon difluoro-halides. Similar reactions are disclosed by R. A. Davis et al. in *J. Org. Chem.*, 32, 3478 (1967) in which up to two bromine atoms in bromofluoroethanes are displaced by reactions with bromine trifluoride. B. M. Regan et al., as disclosed in U.S. Pat. Nos. 3,689,459, 3,773,840 and 3,976,788, used bromine trifluoride to replace one or two chlorine atoms with fluorine at the α-carbon of ethers to make fluorinated ethers.

Applicants have now discovered a unique method for mono-hydrogen and poly-chlorine displacements, especially at the β-carbon to the oxygen, at the same time in either methyl or chloromethyl 1,1,1,3,3,3-hexa-chloro-2-propyl ether using a halogen fluoride such as bromine trifluoride as a multi-substituting and fluorinating agent to produce sevoflurane in as short as one step.

DESCRIPTION OF THE INVENTION

Applicants have found that 1,1,1,3,3,3-hexachloro-2-propanol, a relatively inexpensive compound, may be used as the starting material to prepare sevoflurane in two to four steps. For example, sevoflurane may be produced by reacting 1,1,1,3,3,3-hexachloro-2-propanol and a methylating agent such as dimethyl sulfate in the presence of an aqueous sodium hydroxide solution to yield methyl 1,1,1,3,3,3-hexachloro-2-propyl ether, followed by reacting the latter methyl ether and a halogen fluoride such as bromine trifluoride.

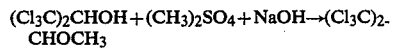

Another suitable methylating agent is methyl iodide.

Alternatively, methyl 1,1,1,3,3,3-hexachloro-2-propyl ether may be converted to the corresponding chloromethyl ether by light induced chlorination in carbon tetrachloride. Reaction of the chloromethyl ether and bromine trifluoride also yields sevoflurane.

It has been found that in order to convert polychlorinated ethers such as $(Cl_3C)_2CHOCH_3$ or $(Cl_3C)_2CHOCH_2Cl$ to sevoflurane directly using bromine trifluoride requires reaction temperatures usually above 20° C. and preferably above 45° C. However, when one or more of the chlorine atoms or the methyl hydrogen atom in $(Cl_3C)_2CHOCH_3$ or $(Cl_3C)_2CHOCH_2Cl$ is replaced by a fluorine atom, the reaction temperature required to make such conversion to sevoflurane drops to as low as 6° C. In general, lower reaction temperatures will improve the reaction yields.

In view of the above, it is advantageous to react methyl or chloromethyl 1,1,1,3,3,3-hexachloro-2-propyl ether with anhydrous hydrogen fluoride in the presence of a catalyst (for example antimony pentachloride) to produce methyl or chloromethyl chlorofluoro-mixed-2-propyl ethers.

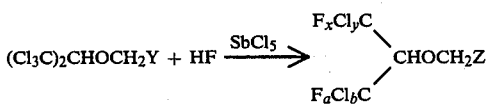

wherein Y=H or Cl, x+y=3, a+b=3, and Z=H, Cl or F, with the proviso that x+a is at least 1.

These methyl or chloromethyl chlorofluoro-mixed-2-propyl ethers may then be reacted with a halogen fluoride (for example bromine trifluoride) to yield sevoflurane.

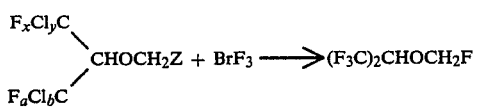

wherein Z=H, Cl or F, x+y=3, a+b=3 and x+a is at least 1.

Such conversion allows recycle of any chlorofluoro-mixed ether intermediates produced in the process of converting methyl or chloromethyl 1,1,1,3,3,3-hexachloro-2-propyl ether to sevoflurane and increases sevoflurane yields.

Other halogen fluorides suitable in the above reactions include ClF, ClF$_3$, BrF, BrF$_3$ and BrF$_5$. Another suitable catalyst is antimony trifluoride, which is believed to react with the fluoride source to generate the active component SbF$_3$Cl$_2$ in the reaction mixture. Other suitable catalysts include chrominum oxide, chromium halide, thorium tetrafluoride, and ferric chloride.

In summary, the discovery of direct conversions of methyl and chloromethyl 1,1,1,3,3,3-hexachloro-2-propyl ethers to sevoflurane in one step, and conversions of the chloro-fluoro mixed ether intermediates having the general formula of (F$_x$Cl$_y$C)(F$_a$Cl$_b$C)CHOCH$_2$Z (where x+y=3, a+b=3, x+a is at least 1 and Z=H, Cl or F) to sevoflurane is advantageous over conventional routes.

The following examples are intended to illustrate, but not to limit, the scope of the invention.

In the examples, gas chromatograms were obtained on an HP5790A Gas Chromatograph (GC) with a thermal conductivity detector at 250° C. detector temperature, 130° C. injection temperature and a helium gas flow of 18 c.c./min. Columns were either ⅛"×20' stainless steel packed with 10% Igepal CO-880 and 15% Ucon LB-550X on 40/60 mesh chromosorb T, temperature at 70° to 175° C., or ⅛"×10' stainless steel packed with 5% OV-17 on 80/100 mesh chromosorb WHP at 40° to 175° C.

Mass spectra by electron impact (EI) technique were obtained from a HP 5995B Gas Chromatograph/Mass Spectrometer (GC/MS) equipped with a direct injection probe and using an electron beam energy of 70 electron volts. Spectra obtained by chemical ionization (CI) technique, which usually provides molecular weight, were obtained on a similar instrument with variable electron beam energy at Rutgers University, New Brunswick, N.J. GC columns used in GC/MS instruments were the same as those for GC analysis.

Proton ($^1$H) Nuclear Magnetic Resonance (NMR) spectra were obtained on either a Varian EM 360 Spectrometer or an IBM AF 270 Fourier Transform Spectrometer. Carbon ($^{13}$C) and fluorine ($^{19}$F) NMR spectra were obtained on an IBM AF 270 Fourier Transform Spectrometer. $^1$H and $^{13}$C NMR chemical shifts were recorded relative to tetramethylsilane. $^{19}$F NMR chemical shifts were recorded relative to fluorotrichloromethane (R-11), negative signs for signals at higher fields then R-11 and positive signs for signals at lower fields than R-11. The $^{13}$C and $^{19}$F NMR spectra were obtained by both proton coupled and proton decoupled modes, however, only proton decoupled data were reported for simplicity.

EXAMPLE 1

Preparation of (Cl$_3$C)$_2$CHOCH$_3$

A 50% NaOH solution, 9.9 g (0.12 mole), was added to a mixture of 33.0 g (0.12 mole) of 1,1,1,3,3,3-hexachloro-2-propanol and 44.5 g (2.47 moles) of water at 0°–10° C. over 30 minutes. This cold mixture was warmed to room temperature and 15.6 g (0.12 mole) of dimethyl sulfate was added slowly at 20°–25° C. over 30 minutes. The reaction mixture was stirred for another 2 hours at room temperature. The crude product was washed with dilute NaOH solution, water and saturated NaCl solution to yield 29.5 g of a colorless liquid. Fractional distillation of the liquid at 93°–93.5° C. and 5 mm Hg gave 26.2 g of the methyl ether at 98.7% purity by GC analysis. This represents a 74.5% yield. The product was purified further by a second distillation to afford greater than 99.6% of purity. Elemental analysis: C$_4$H$_4$Cl$_6$O Calculated C 17.11%, H 1.43%, Cl 75.75%. Found C 17.03%, H 1.43%, Cl 75.31%. $\eta_D^{20}$ 1.5195.

EXAMPLE 2

Preparation of (Cl$_3$C)$_2$CHOCH$_2$Cl

Dry chlorine gas, 4.5 g (0.06 mole), was bubbled at an average rate of 0.1 g/min. into a solution of 10.0 g (0.035 mole) of methyl 1,1,1,3,3,3-hexachloro-2-propyl ether dissolved in 15 ml of carbon tetrachloride illuminated with a 250 watt incandescent lamp at 60° C. maintained by a circulating bath which surrounded the reactor. The reaction progress was monitored by GC. After chlorine was stopped, the reaction mixture was stirred for one hour. The crude product mixture was washed with dilute NaOH solution, water and saturated NaCl solution, and was dried at −20° overnight. After carbon tetrachloride was evaporated, 10.6 g of a colorless liquid containing 55.2% of the desired chloromethyl ether, 3.7% of dichloromethyl ether and 38.9% unreacted methyl ether, was obtained. This corresponds to 52.7% conversion and 90.5% yield based on GC analysis. Fractional distillation of this liquid provided 4.8 g of 93.1% pure chloromethyl ether. A compound of greater than 98% purity was obtained by multiple distillations at 106° C. and 4 mmHg. The product was consistent with the proposed structure when analyzed by GC/MS and $^1$H, $^{13}$C NMR.

(Cl$_3$C)$_2$CHOCH$_2$Cl
MS: EI 195 (M-CCl$_3$), CI 277 (M-Cl)
$^1$H NMR: δ5.0 (s, CHO), δ6.0 (s, OCH$_2$Cl)
$^{13}$C NMR: δ82.0 (s, OCH$_2$Cl), δ93.7 (s, CHO), δ96.2 (s, Cl$_3$C).

EXAMPLE 3

Preparation of sevoflurane from (Cl$_3$C)$_2$CHOCH$_3$

To 2.5 g (0.009 mole) of methyl 1,1,1,3,3,3-hexachloro-2-propyl ether in a Teflon bottle was added dropwise 2 ml (0.04 mole) of liquid BrF$_3$ at 20°–50° C. over 30 minutes. An exotherm was observed and was subsided with an ice water bath. After addition, the reaction mixture was heated at 45°–46° C. for 5 minutes and was then cooled to 0° C. Dilute Na$_2$SO$_3$ solution was added gradually to destroy Br$_2$ and unreacted BrF$_3$. Dilute NaOH solution was then added to neutralize the product solution. The organic was separated and was washed with water and saturated NaCl solution to give 0.6 g of liquid which contained 3% of (CF$_3$)$_2$CHOCH$_2$F (sevoflurane), 59% of $(ClF_2C)(F_3C)CHOCH_2F$ and 29% of $(ClF_2C)_2CHOCH_2F$ by GC analysis and all products were consistent with the proposed structure when analyzed by GC/MS. The sevoflurane was furthermore confirmed to be identical to sevoflurane material prepared by the Regan et al. published route.

EXAMPLE 4

Preparation of sevoflurane from $(Cl_3C)_2CHOCH_2Cl$ BrF$_3$, 2.8 ml (0.06 mole), was added to 3.0 g (0.009 mole) of 94.2% pure chloromethyl 1,1,1,3,3,3-hexachloro-2-propyl ether (contaminated with 5.7% of dichloromethyl ether) at 22°–52° C. by the same procedure as that described in Example 3. The molar ratio of BrF$_3$ to chloromethyl ether was 6.7. The reaction mixture was stirred at 55°–57° C. for 20 minutes and was worked-up in the same manner as Example 3. An organic liquid, 0.2 g, was obtained. GC and GC/MS analyses indicated that this liquid was comprised as follows:

| Compound | Percent |
| --- | --- |
| $(CF_3)_2CHOCH_2F$ (sevoflurane) | 35.3% |
| $(ClCF_2)(F_3C)CHOCH_2F$ | 43.7% |
| $(CF_3)(ClCF_2)CHOCHF_2$ | 7.5% |
| $(ClF_2C)_2CHOCHF_2$ | 6.2% |

EXAMPLE 5

Preparation of sevoflurane from $(Cl_3C)_2CHOCH_2Cl$ from chloromethyl 1,1,1,3,3,3-hexachloro-2-propylether A reaction similar to Example 4 was conducted including 3.0 g (0.009 mole) of 94.2% pure chloromethyl ether and 2.1 ml (0.04 mole) of BrF$_3$ at 21°–57° C. The molar ratio of BrF$_3$ to chloromethyl ether was 4.4. A liquid product, 0.5 g, was obtained containing 4.4% of sevoflurane, 51.7% of $(CF_3)(ClF_2C)CHOCH_2F$, 17.7% of $(ClF_2C)_2CHOCH_2F$, 2.2% of $(CF_3)(ClF_2C)CHOCHF_2$ and 19.7% of $(ClCF_2)_2CHOCHF_2$.

EXAMPLE 6

Preparation of $(ClF_2C)(Cl_2FC)CHOCH_2Cl$ from chloromethyl 1,1,1,3,3,3-hexachloro-2-propylether To a mixture of 6.0 g (0.017 mole) of 87.7% of chloromethyl ether (contaminated with 11.4% of dichloromethyl ether) and 0.9 g (0.0031 mole) of antimony pentachloride in a Teflon bottle was added 5.1 ml (0.25 mole) of anhydrous hydrogen fluoride at 8°–19° C. over 25 minutes. An exotherm was seen and the reaction mixture was cooled by an ice water bath. After addition, the reaction mixture was heated to 55°–56° C. for 10 minutes and was then cooled to 0° C. Aqueous NH$_4$OH solution was slowly added to neutralize unreacted hydrogen fluoride. The organic liquid was washed with water and saturated NaCl solution to give 2.4 g of crude product which as determined by GC and GC/MS comprised the following:

| Compound | Percent |
| --- | --- |
| $(CF_3)(ClCF_2)CHOCH_2Cl$ | 16.4% |
| $(ClF_2C)(Cl_2FC)CHOCH_2Cl$ | 66.7% |
| $(Cl_2FC)_2CHOCH_2Cl$ | 4.7% |
| $(Cl_3C)(Cl_2FC)CHOCH_2Cl$ | 4.2% |

Fractional distillation of the crude product at reduced pressure afforded 0.69 g of greater than 99% pure of $(ClF_2C)(Cl_2FC)CHOCH_2Cl$, b.p. 36°–38° C. at 11 mm Hg, $\eta_{20}{}^D$ 1.4310. Elemental Analysis: $C_4H_3F_3Cl_4O$ Calculated C 18.07%, H 1.14%, F 21.44%, Cl 53.34%. Found C 17.90%, H 1.18%, F 21.65%, Cl 53.38%.

EXAMPLE 7

Preparation of $(Cl_2FC)_2CHOCH_3$

Similar to the procedure in Example 6, 5.0 ml (0.25 mole) of anhydrous hydrogen fluoride was added to a mixture of 4.1 g (0.014 mole) of 98.4% methyl 1,1,1,3,3,3-hexachlora-2-propyl ether and 0.3 g (0.0010 mole) of antimony pentachloride at 15°–30° C. A liquid product (2.4 g) was obtained containing 19.7% of $(Cl_2FC)_2CHOCH_3$ and 70% of $(Cl_2FC)(Cl_3C)CHOCH_3$ as analyzed by GC. Fractional distillation of the crude product at 37°–41° C. at 5 mm Hg gave 0.25 g of 96.6% pure $(Cl_2FC)_2CHOCH_3$. This structure was consistent with the proposed structure when analyzed by GC/MS and $^1H$, $^{13}C$ and $^{19}F$ NMR methods.

$(Cl_2FC)_2CHOCH_3$

MS: EI 211 (M-Cl), CI 247 (M+1)

$^1H$ NMR: $\delta 4.0$ (s, OCH$_3$), $\delta 4.3$ (t, $J_{FCCH}=5.5$ Hz, CHO)

$^{13}C$ NMR: $\delta 64.3$ (s, OCH$_3$), $\delta 92.1$ (t, $J_{FCC}=24.4$ Hz, CHO), $\delta 118.4$ (d, $J_{FC}=307.5$ Hz, Cl$_2$FC)

$^{19}F$ NMR: $\delta 59.6$ (s).

EXAMPLE 8

Preparation of sevoflurane from $(ClF_2C)(Cl_2FC)CHOCH_2Cl$

Following the same procedure as in Example 4, 0.6 ml (0.012 mole) of BrF$_3$ was added at 10°–44° C. to 1.3 g (0.0047 mole) of 96.2% pure $(ClF_2C)(Cl_2FC)CHOCH_2Cl$. The product collected (0.5 g) contained 0.5% of sevoflurane, 29.1% of $(F_3C)(ClF_2C)CHOCH_2F$ and 63.7% of $(ClF_2C)_2CHOCH_2F$ as determined by GC analysis.

EXAMPLE 9

Preparation of sevoflurane from $(Cl_2FC)_2CHOCH_3$

Following the same procedure as in Example 4, 0.75 ml (0.015 mole) of BrF$_3$ was added to 1.12 g (0.0032 mole) of 70.3% of $(Cl_2FC)_2CHOCH_3$ (contaminated with 22.8% of $(Cl_2FC)_2CHOH$ and 5% of $(Cl_3C)(Cl_2FC)CHOCH_3$) at 6°–52° C. Organic crude product (0.26 g) was recovered after reaction containing 8.0% of sevoflurane, 51.3% of $(F_3C)(ClF_2C)CHOCH_2F$ and 31.0% of $(ClF_2C)_2CHOCH_2F$ as analyzed by GC and GC/MS.

EXAMPLE 10

Preparation of $(ClF_2C)_2CHOCH_2F$

Similar to Example 8, 1.1 g (0.004 mole) of 95.7% pure $(ClF_2C)(Cl_2FC)CHOCH_2Cl$ was reacted with 0.4 ml (0.008 mole) of BrF$_3$ at 9°–31° C. to give 0.48 g of crude product which was comprised of the following:

| Compound | Percent |
| --- | --- |
| sevoflurane | 0.1% |
| $(F_3C)(ClF_2C)CHOCH_2F$ | 11.6% |

| -continued | |
|---|---|
| Compound | Percent |
| $(ClF_2C)_2CHOCH_2F$ | 85.9% |

Molecular distillation at an oil temperature of 80°–88° C. of the crude product at atmospheric pressure gave 0.084 g of 93.6% pure $(ClF_2C)_2CHOCH_2F$ of which the structure was determined by GS/MS, $^1H$, $^{13}C$ and $^{19}F$ NMR methods.

$(ClF_2C)_2CHOCH_2F$

MS: EI 213 (M-F), CI 233 (M+1)

$^1H$ NMR: δ4.5 (quintet, $J_{FCCH}=7$ Hz, CHO), δ5.5 (d, $J_{FCH}=55$ Hz $OCH_2F$)

$^{13}C$ NMR: δ82.1 (quintet, $J_{FCC}=28.5$ Hz, CHO), δ103.2 (d, $J_{FC}=226.7$ Hz, $OCH_2F$), δ124.4 (d, $J_{FC}=298.0$ Hz, $ClF_2C$)

$^{19}F$ NMR: δ−153.4 (s, $OCH_2F$), two non-equivalent fluorines on $ClF_2C$ at δ−61.6 (d, $J_{FCF}=188.0$ Hz) and δ−58.6 (d, $J_{FCF}=188.0$ Hz)

EXAMPLE 11

Preparation of $(Cl_2FC)_2CHOCH_2Cl$

Following the same procedure as in Example 6, 12.5 ml (0.62 mole) of anhydrous hydrogen fluoride was added to a mixture of 16.4 g (0.046 mole) of 89.4% pure $(Cl_3C)_2CHOCH_2Cl$ and 1.89 g (0.0063 mole) of antimony pentachloride at 1°–47° C. After work-up, a crude product (11.7 g) was obtained containing 4.5% of $(ClCF_2)_2CHOCH_2Cl$, 62.3% of $(ClF_2C)(Cl_2FC)CHOCH_2Cl$, 20.2% of $(Cl_2FC)_2CHOCH_2Cl$ and 2.3% of $(Cl_3C)(Cl_2FC)CHOCH_2Cl$ as determined by GC analysis. After fractional distillation of the crude at 35 mm Hg and 88° C., a residue (3.8 g) remained containing 66.3% of $(Cl_2FC)_2CHOCH_2Cl$ and 8.6% of $(Cl_3C)(Cl_2FC)CHOCH_2Cl$. This residue was re-distilled 3 times to give 0.47 g of 98.4% pure of $(Cl_2FC)_2CHOCH_2Cl$ at 58°–59° C. at 3.5 mmHg. $\eta_D^{20}$ 1.4625. Elemental analysis: $C_4H_3F_2Cl_5O$ Calculated C 17.02%, H 1.07%, F 13.46%, Cl 62.78%. Found: C 17.23%, H 1.15%, F 13.47%, Cl 62.74%.

EXAMPLE 12

Preparation of $(Cl_3C)(Cl_2FC)CHOCH_3$

Following the same procedure as in Example 6, 6.5 ml (0.32 mole) of anhydrous hydrogen fluoride was added to a mixture of 5.1 g (0.018 mole) of 97.3% methyl 1,1,1,3,3,3-hexachloro-2-propyl ether and 0.86 g (0.0029 mole) of antimony pentachloride at 10°–30° C. 3.6 g of crude organic product containing 28.6% of $(Cl_3C)(Cl_2FC)CHOCH_3$ and 68.2% unreacted starting material, was obtained. Fractional distillation of this crude product at 58°–65° C. at 5 mm Hg provided 1.0 g of greater than 96% pure $(Cl_3C)(Cl_2FC)CHOCH_3$. $\eta_D^{20}$ 1.4795. Elemental analysis: $C_4H_4FCl_5O$ Calculated: C 18.18%, H 1.52%, F 7.19%, Cl 67.06%. Found: C 18.02%, H 1.50%, F 7.40%, Cl 67.18%.

EXAMPLE 13

Preparation of $(ClF_2C)_2CHOCH_2Cl$

Following the same procedure as in Example 6, 5.5 ml (0.27 mole) of anhydrous hydrogen fluoride was reacted with 6.2 g (0.018 mole) of 94.4% pure $(Cl_3C)_2CHOCH_2Cl$ and 0.75 g (0.0025 mole) of antimony pentachloride at 7°–44° C. A crude product (3.45 g) was collected comprised the following:

| Compound | Percent |
|---|---|
| $(ClF_2C)_2CHOCH_2Cl$ | 11.8% |
| $(ClF_2C)(Cl_2FC)CHOCH_2Cl$ | 75.4% |
| $(Cl_2FC)_2CHOCH_2Cl$ | 4.2% |
| $(Cl_3C)(Cl_2FC)CHOCH_2Cl$ | 1.4% |

Fractional distillation of this crude product at 40 mm Hg and 57°–64° C. gave 0.3 g of greater than 86% pure $(ClF_2C)_2CHOCH_2Cl$. This structure was determined by GC/MS, $^1H$ and $^{19}F$ NMR methods.

$(ClF_2C)_2CHOCH_2Cl$

MS: EI 247 (M−1), CI 249 (M+1)

$^1H$ NMR: δ4.6 (quintet, $J_{FCCH}=6.0$ Hz, CHO), δ5.7 (s, $OCH_2Cl$)

$^{19}F$ NMR: two non-equivalent fluorines on $ClF_2C$ at δ−60.2 (d, $J_{FCF}=180.3$ Hz) and δ−57.4 (d, $J_{FCF}=180.3$ Hz)

The above described processes can be carried out batch or continuous. In a continuous process, continuous recycle of the mixed fluoro-chloro derivatives is readily accomplished by distillation, as will be evident to those skilled in the art, since the fully fluorinated compounds have the lowest boiling points.

While there has been described what are at present considered to be preferred embodiments of the invention, it will be understood that various modifications may be made therein which are within the true spirit and scope of the invention as defined by the following claims:

We claim:

1. A method for the preparation of fluoromethyl 1,1,1,3,3,3-hexafluoro-2-propyl ether comprising reacting methyl 1,1,1,3,3,3-hexachloro-2-propyl ether of or chloromethyl 1,1,1,3,3,3-hexachloro-2-propyl ether with chlorine trifluoride or bromine trifluoride.

2. The method of claim 1, wherein the halogen fluoride is $BrF_3$.

* * * * *